United States Patent [19]

Speranza

[11] Patent Number: 5,206,818
[45] Date of Patent: Apr. 27, 1993

[54] FUGITIVE EMISSIONS MONITORING SYSTEM INCLUDING INTEGRATED FUGITIVE EMISSIONS ANALYZER AND SOURCE IDENTIFIER

[75] Inventor: Paul A. Speranza, Endicott, N.Y.

[73] Assignee: International Business Machines Corporation, Armonk, N.Y.

[21] Appl. No.: 762,194

[22] Filed: Sep. 19, 1991

[51] Int. Cl.[5] ............................................. G06F 15/74
[52] U.S. Cl. .................................... 364/550; 73/23.2; 73/40.5 R
[58] Field of Search ....................... 73/23.2, 31.01, 40, 73/40.5 R; 364/550, 496

[56] References Cited

U.S. PATENT DOCUMENTS

| | | | |
|---|---|---|---|
| 4,394,567 | 7/1983 | Schonhuber | 235/375 |
| 4,788,849 | 12/1988 | Yonemura et al. | 73/40.5 R X |
| 4,800,512 | 1/1989 | Busch | 364/551.01 |
| 4,935,875 | 6/1990 | Shah et al. | 364/497 |
| 5,099,437 | 3/1992 | Weber | 364/550 |

FOREIGN PATENT DOCUMENTS

| | | | |
|---|---|---|---|
| 1062042 | 9/1979 | Canada . | |
| 107752 | 5/1991 | Japan | 73/23.2 |

OTHER PUBLICATIONS

"Recommending an Improved Method for Monitoring and Estimating Fugitive Emissions", Xang, Xu, 1988, vol. 10 Environment Monit. Assess.
"Use of Portable Instrumentation for the Monitoring of Fugitive Organic Emissions From Hazardous Waste Incinerators", Summers, C. H. et al, EPA Report, 1984.
"The Measurement and Importance of Fugitive Emissions", Jones, A. L., Ann. Occup. Hyg. 1984, vol. 28, #2.
"Evaluation of Developmental Industrial Hygiene Instrumentation at the University of Minnesota-Duluth Gasifier", Schuresko, D. D. et al, Oak Ridge National Laboratory Report, 1983.
"Evaluation of Potential VOC Screening Instruments", Menzies, K. T. et al, US Environ. Prot. Agency, Res. Dev. 1983.
"Response Factors for VOC Analyzers Used in Fugitive Emission Monitoring", G. E. Harris et al, 1982, vol. 1, Ann Arbor Sci.
"Development of Horizontal Elutriators for Sampling Inhalable Particulate Fugitive Emissions", Cushing, K. M. U.S. Environ. Prot. Agency, Off. Res. Dev. 1980.
"Fugitive Emissions Detection, Distribution and Reduction", Delaney, B., 1981, Control Technol. Plast. Resins Ind.
"Measurement and Control of Fugitive Hydrocarbon Emissions", 1980, vol. 1, U.S. Dept. Energy Environ. Control Symposium.

(List continued on next page.)

Primary Examiner—Hezron E. Williams
Assistant Examiner—Joseph W. Roskos
Attorney, Agent, or Firm—Richard M. Goldman

[57] ABSTRACT

Disclosed is a method and system for monitoring fugitive emissions in a multi-source fugitive emission environment. The system includes machine readable elements (as bar code) at each fugitive emissions source. These machine readable elements are for identifying the source. The system also has a portable monitor that includes a reader, a detector, and storage. Specifically, the reader reads the machine readable element and generates a machine storable source identification signal corresponding to the element. The detector generates a second machine storable signal. This signal represents the amount or other attribute of fugitive emissions from the fugitive emissions source. Finally, the portable monitor includes storage for storing the source identification signals and the fugitive emissions signals. The portable monitor is used in conjunction with or may even include a computer. The computer stores identification signals and the fugitive emissions signals and tracks the amount of fugitive emissions by source.

3 Claims, 3 Drawing Sheets

OTHER PUBLICATIONS

"Detecting, Locating and Measuring of Organic Chemical Fugitive Emissions", Lawes, H., 1980, Int. Environ. Safety.

"Fugitive Hydrocarbon Emissions–Measurement & Data Analysis Methods", Hanzevack, K. M. 1978, U.S. Environ. Pro. Agency, Off. Res. Dev.

"Experimental Techniques for the Determination of Fugitive Hydrocarbon Emissions", Air Pollut. Control. Assoc. 1978, vol. 71st, vol. 3, W. S. Eaton et al.

"The Measurement of Fugitive Hydrocarbon Emissions From Selected Sources in Petroleum Refineries", Rosebrook et al, Air Pollut. Control Assoc., 1978, vol. 71st. vol. 3.

"Measuring Fugitive Emissions From Petrochemical Plants", Hughes, T. W. et al, 1979, vol. 75, #8, Chem. Eng. Prog.

"Detection and Classification of Fugitive Component Leaks", Harrison, P. R. 1978, U.S. Environ. Prot. Agency Off. Res. Dev.

"Fugitive Hydrocarbon Emissions–Measurement and Data Analysis Methods", Hanzevack, K. M., U.S. Environ. Prot. Agency, Off. Res. Dev. 1978.

SOURCES DESCRIPTER TABLE

| BARCODE | TYPE | SYSTEM 1 | SYSTEM 2 | SYSTEM | CONTENTS | PRESS | TEMP |
|---|---|---|---|---|---|---|---|
| 1100001 | VALVE | PLANT 1 | SOLVENT RECOVERY | | CHCl3 | 1.3 ATM | 27C |
| 1100010 | VLV SEA11 | PLANT 1 | SOLVENT RECOVERY | | CHCl3 | 1.3 ATM | 27C |
| 1100011 | VLV SEA12 | PLANT 1 | SOLVENT RECOVERY | | CHCl3 | 1.3 ATM | 27C |
| 1100011 | FLANGE | PLANT 1 | SOLVENT RECOVERY | | CHCl3 | 1.3 ATM | 27C |

SAMPLES TABLE

| BARCODE | DATE | TIME | TEMP | PPMV |
|---|---|---|---|---|
| 1100001 | 910908 | 0805 | 27 | 127 |
| 1100010 | 910908 | 0807 | 27 | 315 |
| 1100011 | 910908 | 0808 | 27 | 208 |
| ... | | | | |
| 1100001 | 910811 | 0812 | 29 | 126 |
| 1100010 | 910811 | 0814 | 28 | 317 |
| 1100011 | 910811 | 0817 | 28 | 210 |
| ... | | | | |
| 1100001 | 910714 | 0812 | 29 | 124 |
| 1100010 | 910714 | 0814 | 28 | 314 |
| 1100011 | 910714 | 0817 | 28 | 205 |

REPORT TABLE

REPORT FOR VALVE 1100001

| DATE | PPMV |
|---|---|
| 910908 | 127 |
| 910811 | 126 |
| 910707 | 124 |

FIG.3

FUGITIVE EMISSIONS MONITORING SYSTEM INCLUDING INTEGRATED FUGITIVE EMISSIONS ANALYZER AND SOURCE IDENTIFIER

FIELD OF THE INVENTION

The invention relates to a fugitive emissions monitoring system including an integrated fugitive emissions analyzer and source identifier. Fugitive emissions are the very large number of very low emission rate emissions from an industrial complex. These fugitive emissions include emissions from valves, pumps, seals, gaskets, flanges, fittings, hoses, and the like. Regulatory requirements and sound operating practices require extensive monitoring and record keeping to identify, track, and correct fugitive emissions. This extensive monitoring and record keeping takes the form of (1) unique identification of each potential emission source, for example, each valve, pump, seal, gasket, flange, fitting, hose, or the like, and (2) periodic, for example, daily, weekly, or monthly monitoring of each such potential source.

According to the disclosed invention each potential source has identifying means capable of providing electronic storage of a source location identifier substantially simultaneously with sampling and electronic storage of the sampled data. This identifying means, which may be bar code label, is read by a detector, which may be a bar code reader, and the gas in proximity thereto is substantially sampled by a suitable sensor. These two inputs, the source identifier and the gas chemistry, are stored in an electronic data logger for subsequent up loading and analysis in a computer.

BACKGROUND OF THE INVENTION

1. Air Pollution

Air pollution exists when the atmosphere contains an objectionable concentration of one or more deleterious substances. A substance may be deleterious because it is an irritant. For example, it may be irritating to the eyes, nose, skin, or mucus membranes of the respiratory system, or may even cause difficulties in breathing.

In other cases pollutants may be toxic, causing chronic or acute reversible or irreversible physiological damage to humankind, animals, or vegetation. Ultimately this includes serious disease processes, such as black lung disease, brown lung disease, and malignancies. In some case pollutants may even lead to extermination of species.

Other effects of air pollution include deterioration of materials of construction and of structures, or the creation of areas where certain plant species cannot survive.

The atmosphere has always served as a gaseous and vapor waste dispersion medium and disposal area. Waste materials, in the form of fogs, dispersions, particulates, combustion products, and the like, are introduced into the air, become widely dispersed, diluted, hydrated, and even photochemically reacted. Some of these products then settle to the ground or are removed by precipitation. The precipitation and particulates may themselves be harmful. Other products may stay dispersed in the atmosphere, building up, and causing further problems.

Human activities, especially industrial activities, have added both new pollutants to the atmosphere and increased the background concentrations of pollutants to a very high degree. Synthetics, acidic combustion products, as $SO_2$, and photodissociable synthetic molecules, as chlorofluorocarbons, have been added to the ecological load by human industrial activities.

2. Ambient Air Quality Standards

Ambient air quality standards are designed to protect the atmosphere from air pollution.

Air pollution has three components: (1) source emissions, (2) atmospheric transport and dispersal, and (3) receipt by a receptor. The degree of an air pollution problem depends upon the interaction of these components.

Time is an important factor in each of the three components of air pollution. In the case of the source, for example, emissions are continuous from a power plant but intermittent from a dry cleaning plant. In the case of atmospheric transport, inversions, stationary fronts, and atmospheric high pressure systems which remain over a region for several days all reduce dispersion. This reduced dispersion can produce air pollution episodes during which pollutant concentrations build up. For receptors, duration of exposure to pollutants is important. Humans may survive large dosages of some pollutants and then eliminate the pollutant from their bodies. However, other pollutants can accumulate in the body over time, and are only respirated or excreted with great difficulty, eventually causing illness or death. For these reasons, standards for air pollutant concentrations specify an averaging period of from minutes to a year.

In the case of emission standards, as distinguished from time-averaged concentration standards, some emission standards are also set with time limitations. For example, plume opacity standards which allow a certain period of time for start-up and maintenance operations.

If pollutants are allowed to enter the air, nationwide and worldwide emissions over a period of years may cause an increase in the background concentration of that pollutant. This may create a condition in which new normal concentrations, which are higher then old normal concentrations, either interfere with normal atmospheric processes, as is the case with the "Greenhouse Effect," the polar holes in the ozone layer, and acid rain, or the new "background" of the pollutant may itself be directly deleterious to human health. Ambient air quality standards are intended to limit the concentration of pollutants.

3. Sources

Sources are the pollutant emitters. As a first approximation, sources can be treated individually as point sources. Point sources include each stack at a power plant, or petroleum refinery. Alternatively, or additionally, sources may be treated collectively as area sources, for example, all of the automobile exhausts in a metropolitan area.

Pollutants can be emitted from sources as gases or aerosols, that is, mist, smoke, soot, fume, and dust. Once in the atmosphere, the primary pollutant may undergo transformation into a secondary pollutant, for example, the oxidation of sulfur dioxide to sulfates or the ultraviolet scission of chlorofluorocarbons to free radicals.

4. Fugitive Sources

Emissions from a source generally enter the atmosphere from a distinct stack or exhaust pipe, as an exhaust pipe or stack. While mobile sources, that is, automobiles, and large stationary sources ranging from power plant and industrial stacks down to residential chimneys emit most of the man-made pollutants, pollutants also originate from a very large number of very small, diverse locations around a building, a piece of equipment, a dusty road, or a storage pile These are called fugitive emissions.

Fugitive industrial emissions are another source of pollutants. This is especially true in the case of solvents, halocarbon vapors, cleaning fluids, refrigerants, and the like, as well as radioactive emissions. Fugitive emissions may escape into the atmosphere through windows, vents, and doors rather than through regular exhaust systems. Rosebrook et al. "The Measurement of Fugitive Hydrocarbon Emissions from Selected Sources in Petroleum Refineries," *Proceedings, Annual Meeting—Air Pollution Control Association,* 1978, 71st, Volume 3, Paper 78-36.4, 15 pp., CA:92:168224z, present relative fugitive emission data for hydrocarbon sources, such as valves, flanges, pump seals, compressor seals, and drains at four typical petroleum refineries. They report that compressor seals have the highest average leak rates, while leakage from flanges are practically insignificant. They also report that because of their large numbers, the highest total leakage is from valves.

Hanzevack et al, "Fugitive Hydrocarbon Emissions—Measurement and Data Analysis Methods," U.S. Environmental Protection Agency Office of Research and Development, EPA 1978, EPA-600/2-78-199, Proceedings: Symposium/Workshop On Petroleum Refinery Emissions; PB-287 900, 41-54, CA:93: 172919t, presents data on valve fugitive emissions at a petrochemical plant. Fugitive emissions are correlated with maintenance, and is reported to show emission reduction through improved maintenance.

While each individual fugitive emission is likely to be small, the total outflow from fugitive emissions is likely to be quite large. The identification and measurement of fugitive emissions is required for both emission inventorying and subsequent pollution control efforts.

5. Fugitive Sources and the Emission Inventory

An important requirement for any air pollution control program is a comprehensive emission source inventory. This inventory identifies sources, source locations, pollutant types, and quantities of emissions throughout the relevant areas. A further aspect of the emission source inventory, especially if mathematical modeling of pollutant dispersion is contemplated, includes such engineering information as source heights, diameters, capacities, and pollutant stream constituents, exit velocities, temperatures, and concentrations. These data are used to model the plume emanating from the source.

Data for the emission inventory may be gathered from plant surveys, consumption summaries, production information, and stack-sampling reports.

6. Fugitive Halocarbon Emissions

Halocarbon emissions, including fluorocarbon, chlorocarbon, and chlorofluorocarbon emissions, occur from a number of sources, including, among others, purification system vents, product-loading vents, hoods, vents, stacks, joints, seals, fittings, gaskets, and valves, including relief valves. In practice, fugitive emissions, once identified and located, are minimized by, among other expedients, repair, replacement, or even enclosure of the emission sources and collection of the emissions.

Other expedients for the control of halocarbon fugitive emissions include: installation of primary and redundant incineration facilities for both point-source and collected fugitive emissions; installation of scrubbing and neutralization or recovery units in conjunction with the incinerators; installation of closed-process sewers, collection systems and larger or redundant wastewater strippers; replacement of single mechanical seals on pumps and agitators with double mechanical seals; leak-detection systems and portable monitors; enclosed sampling and analytical systems; and vapor-recovery systems for halocarbon loading, unloading, and equipment clearing.

7. Measurement of Fugitive Emissions

Pollution measurements are divided into two categories: ambient measurements and source measurements. Pollution measurements, whether source measurements or ambient measurements, often require detection and measurement in the ppmv to ppbv (parts per million by volume to parts per billion by volume) range. This is especially true to determine trends. As a general rule source concentrations range from tenths of a percent to a few hundred ppmv, and ambient concentrations are lower.

In metropolitan areas of high population density and in highly integrated manufacturing facilities, extensive sampling networks have been established. These networks use continuous monitors installed at strategic locations the data transmitted to a common repository or processor.

Ambient air sampling is typically used to:

(1) establish and operate a pollution incident alert network, (2) locating the source of an undesirable pollutant, (3) obtaining permanent sampling records for legal action, (4) monitor a stationary emission source, (5) model changes in the system, and (6) establish long term trends.

Source sampling differs markedly from ambient sampling and has unique problems and techniques which are distinct and different from ambient sampling. Source gas temperatures may be high and the raw source gas may contain high concentrations of water vapor or entrained mist, dust, or other interfering substances. The high temperatures may require specialized techniques and equipment, while the particulates and gases may deposit on, or be absorbed in, or otherwise interfere with the sampling probes before reaching the sensor.

A primary objective of source sampling is to prove compliance with regulations. Other objectives of source sampling are to provide emission data and emission data trends, and in this way to determine the need for maintenance of process or control equipment, and measure product loss. In the case of large stationary sources continuous sampling is utilized, and this sampling may be under the control of a central processor. However, in the case of an industrial complex with miles of process piping with instrumentation, and many valves, fittings, elbows, and flanges, sampling is typically infrequent, occasional, or intermittent. This is especially so in the case of sampling fugitive emissions.

Gaseous fugitive emissions, like all gaseous pollutants, are detected by their chemical nature. In the case of halocarbon and hydrocarbon gas fugitive emissions techniques such as gas chromatography, flame ionization, photo ionization, infrared techniques, and the like are typically used.

Typically, volatile organic compound detection systems operate on photoionization and infrared principles in the concentration ranges of from less then 100 ppmv to more then 10,000 ppmv. Volatile organic compound detectors are described, for example, by Menzies, K. T. et al, "Evaluation of Potential VOC Screening Instruments," U.S. Environ. Prot. Agency, Res. Dev., (Rep), EPA, 1983, EPA-600/9-83-003, Incineration Treat. Hazard. Waste: Proc. Annual Res. Symp., 8th; PB83-210450, pp. 143-158, CA:100:161189s. Other volatile organic compound detectors include flame ionization detectors, as described, for example in Summers, C. H. et al., k"Use of Portable Instrumentation For the Monitoring of Fugitive Organic Emissions from Hazardous Waste Incinerators," Report, 1984, EPA-600/2-84-103, CA:102:11494q, and Lawes, H., "Detecting, Locating, and Measuring of Organic Chemical Fugitive Emissions," Int. Env. Saf., 1980 (Apr.), pp. 7-10, CA:93:209408d.

For fugitive emission sampling purposes, the measurement may require the determination of the temperature, concentration, and characteristics of the gas contaminants. Adequate data collection also requires the mass rates of emission of each contaminant. This requires that concentration and volumetric flow rate data be taken.

Fugitive industrial emissions are typically sampled in the air space around fittings, pumps, valves, flanges, hoods, small stacks, and the like. Most commonly fugitive industrial emissions are non-condensable hydrocarbons and halocarbons, relatively free of particulates. In the sampling of noncondensable gases free of particulates, the gases are extracted by a single-point grab sample, a single-point integrated sample, or a multipoint integrated sample. Typically, the sampling probe is fabricated of stainless steel, borosilicate, quartz glass, aluminum, copper, or Teflon. The sample is drawn into the sample probe by a one-way squeeze bulb that is attached to the probe. A glass or Pyrex-wool filter may be inserted in the probe tip to remove any unwanted particulates.

In more elaborate systems a pump first sucks the gas through a cold trap. This dries the gas. Then the gas is drawn through a rotameter to measure flow rate, and into the analytical apparatus.

Fugitive emission sampling and monitoring is by its very nature a laborious, labor intensive, time consuming process. Because of the large number of sources, that is, every pipe, valve, flange, gasket, hood, stack, and vent, it is not practical to provide constant, on-line, real time monitoring, with either scanned data capture or interrupt driven data capture. To the contrary, it has been necessary to take gas sampling equipment to each potential fugitive gas emissions source, individually identify the source, for example by entering the source identifier on a keyboard or numeric pad, and individually sample the source. Source sample results would then be manually entered, for example, again using a keyboard or numeric pad. The possibility of human error is high, especially in inclement weather or at relatively inaccessible sites in a factory.

Thus, a need exists for a simple system that can identify a fugitive emission to a specific source, store the source identifier and the emission rate, and correlate the collected data.

OBJECTS OF THE INVENTION

It is one object of the invention to provide a simple method and system for identifying potential fugitive emission sources, measuring and storing the fugitive emission data, as concentration or radioactivity, and correlating the fugitive emissions with, for example, previous fugitive emissions data from the same source or other sources.

It is a further object of the invention to provide a method and system that allows for comparison of fugitive emission data by commodity, across commodities, by source, across sources for a given time, or by time series for a given source.

SUMMARY OF THE INVENTION

According to the invention there is provided a method and system for monitoring fugitive emissions in a multi-source fugitive emission environment, for example a complex manufacturing facility.

The method and system integrate (1) machine readable source identification elements at each fugitive emissions source, with (2) a means of reading these source identification elements, with (3) a means of sampling fugitive emissions at the identified source, and with (4) a means of correlating the source identification with the concentration, radioactivity, or some other attribute of the sampled fugitive emission.

The machine readable elements are for identifying the source, and may be a simple as bar code stickers. Alternatively, they may be individual ROMs with such identification as part number, location, and gas carried.

The system also has a portable monitor that includes a reader, a detector, and storage. Specifically, the reader reads the machine readable element and generates a machine storable source identification signal corresponding to the element.

In a preferred exemplification of the invention the machine readable identification means at the fugitive emissions source is a bar code. The reader is responsive to the bar code. That is, it reads the bar code and generates a machine storable source identification signal corresponding to the bar code.

The detector generates a second machine storable signal. This signal represents, for example, the amount or some other attribute of fugitive emissions from the fugitive emissions source.

The fugitive emissions are generally organic vapor fugitive emissions and the fugitive emission detection means is a volatile organic compound detector. Typical volatile organic compound detectors include photo ionization detectors, flame ionization detectors, infrared absorbtion detectors, and combinations of these detectors.

Finally, the portable monitor includes storage for storing the source identification signal and the fugitive emissions signal. The portable monitor is used in conjunction with or may even include a computer. The computer stores identification signals and the fugitive emissions signals and tracks the amount of fugitive emissions by source. The computer is able to sort the fugitive emission sources by an attribute of the fugitive emissions, for example, source, time, quantity, or composition.

In a preferred exemplification the system includes a display. This display displays data for a plurality of fugitive emission sources, and preferably is capable of selecting individual fugitive emissions sources, and displaying a signal corresponding to the amount of fugitive emissions detected at each such selected source.

Various physical configurations of the system are possible. For example, the portable monitor and the computer may be a single unit. Alternatively, they may be separate units.

The system and method of the invention provides a simple system for identifying potential fugitive emission sources, measuring and storing the fugitive emission rate, and correlating the fugitive emission with, for example, previous fugitive emissions from the same source or other sources.

The system and method of the invention also provide a means of comparing fugitive emission rates by commodity, across commodities, by source, across sources for a given time, or by time series for a given source.

THE FIGURES

The method and system of the invention may be understood by reference to the FIGURES appended hereto.

FIG. 3 is a representation of relational data base tables obtainable from the system of the invention.

DETAILED DESCRIPTION OF THE INVENTION

According to the invention there is provided a method and system for monitoring fugitive emissions in a multi-source fugitive emission environment, for example a complex manufacturing facility. Such sites are characterized by thousands of potential fugitive emission sources. These potential emission sources must be monitored periodically for both regulatory and maintenance purposes. The system is a complete, automated package for monitoring fugitive emissions.

The method and system integrate (1) machine readable unique source identification elements at each fugitive emissions source, with (2) a means of reading these unique source identification elements, (3) a means of sampling fugitive emissions at the identified source, and (4) a means of correlating the source identification with the concentration, radioactivity, or other attribute of the sampled fugitive emission.

Figure 1:
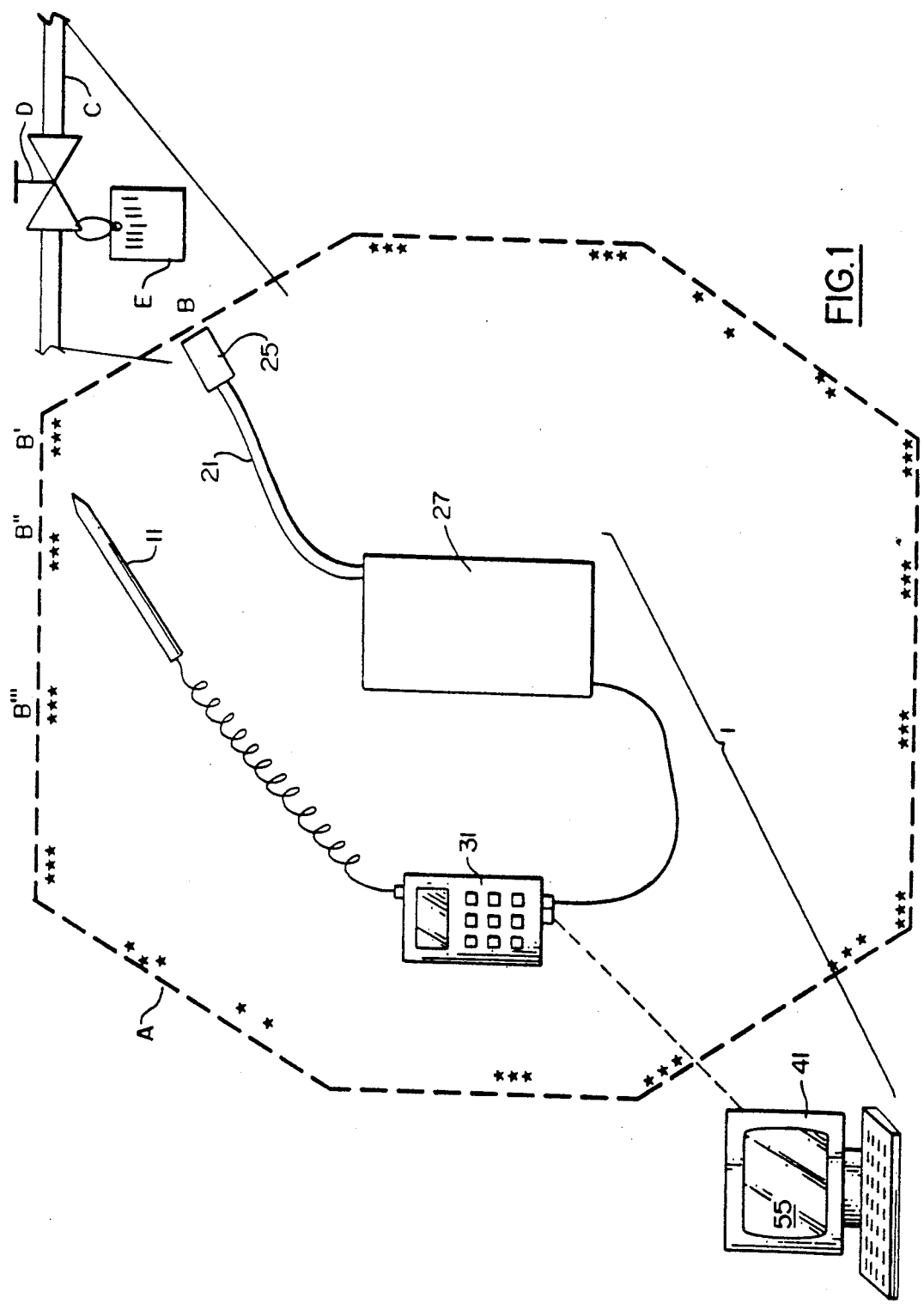
FIG. 1 is a schematic overview of one exemplification of the system and method of the invention.

FIG. 1 shows one exemplification of the invention. The system 1 shown in FIG. 1 is intended to function in a multiple fugitive emission source environment A having a plurality of potential fugitive emission sources B', B'', B''', ..., B$^n$. One such fugitive emission source, B, is a pipeline C, with a control valve D, having a bar code label, E, associated therewith. The bar code label, E, carries the component identification number that is unique to the component, D. This unique identification number is usable for maintenance logging as well as emissions logging.

The system 1, has an input means to read the identification indicia on the source, B. This input means is illustrated as a bar code reader 11 intended to co-operate with the bar-code label, E, extending from the control valve, D. The bar code reader 11 may be a scanner, a wand, or a non-contact laser, as is well known in the bar code reader art.

The system, 1, further includes a sesnor, as a subatomic particle counter for radioactive emissions, or a "sniffer" system for organic emissions. A "sniffer" system 21 is shown having an organic vapor analyzer (OVA) tube 25, and an organic vapor analyzer 27. The organic vapor analyzer may be a Foxboro 108 TM organic vapor analyzer or equivalent. Vapor analyzers 27 typically have an analog output and require either an analog/digital convertor (not shown) or a datalogger with analog to digital conversion means.

The datalogger 31 is capable of receiving a signal from the bar code reader 11 and also a signal from the organic vapor analyzer 21 and converting these signals into machine storable signals that can be stored for future reference and analysis. One such datalogger is an OMNIDATA POLYCORDER TM.

In the system shown in FIG. 1 the data stored in the datalogger 31 maybe periodically uploaded to a digital computer 41 for storage and analysis. The data may be stored in a data base or a relational data base, where, for example, the source identification from the barcode label E provides the relation between the measured sample attribute and system and stored sample attributes. Typical stored system attributes include engineering and construction data relating to the fugitive emission source, for example, maintenance history, installation history, materials of construction, gas contained in the system, gas temperature, gas pressure, and gas flow rate. Typical stored sample data include leakage history over previous samples from the same source.

In the exemplification shown in FIG. 1 the datalogger 31 is separate and distinct from digital computer. In the exemplification shown in FIG. 2 the data logger 31 and the digital computer 41 are contained in a single unit 42.

The machine readable elements E are for identifying the source, and may be a simple as bar code stickers. Alternatively, they may be individual ROMs with such identification as part number, location, and gas carried.

The reader 11 reads the machine readable element E and generates a machine storable source identification signal corresponding to the element E.

In a preferred exemplification of the invention the machine readable identification element E at the fugitive emissions source D is a bar code label E. The reader 11 is responsive to the bar code. That is, it reads the bar code and generates a machine readable or machine readable and storable source identification signal corresponding to the bar code. This source identification signal is stored in the datalogger 31, for example, for direct use or for future uploading to a digital computer 41.

The detector 21, also referred to as a sensor or a "sniffer" generates a second machine storable signal. This signal represents, for example, the amount or some other attribute of fugitive emissions from the fugitive emissions source D.

The fugitive emissions are generally organic vapor fugitive emissions and the fugitive emission detection means, that is, the sniffer or sensor, 21, is a volatile organic compound detector, also referred to as an organic vapor analyzer. Typical volatile organic compound detectors include photo ionization detectors, flame ionization detectors, infrared absorbtion detectors, and combinations of these detectors.

Finally, the portable monitor includes a datalogger 31 or other storage device for storing the source identification signal and the fugitive emissions signal. The portable monitor is used in conjunction with or may even include a computer 41. The computer 41 stores identification signals and the fugitive emissions signals and tracks the amount of fugitive emissions by source. The computer 41 is able to sort the fugitive emission sources by an attribute of the fugitive emissions, for example, source, time, quantity, or composition.

In a preferred exemplification the system includes a display 55. The display 55 displays data for a plurality of fugitive emission sources, and preferably is capable of selecting individual fugitive emissions sources, and displaying a signal corresponding to the amount of fugitive emissions detected at each such selected source.

Figure 2:
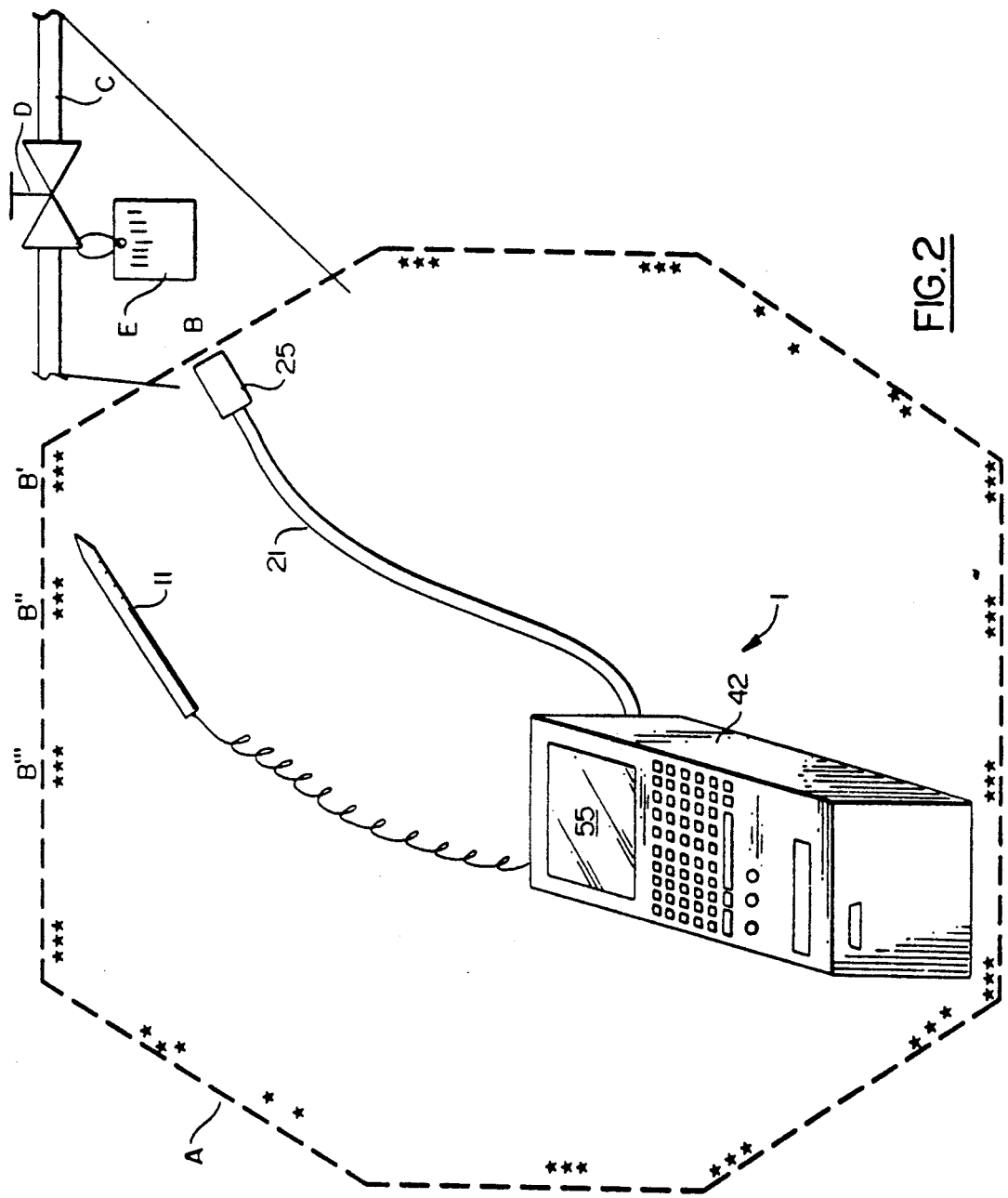
FIG. 2 is a schematic overview of an alternative exemplification of the system and method of the invention.

Various physical configurations of the system are possible. For example, they may be separate units as shown in FIG. 1. Alternatively, the portable monitor and the computer may be a single unit 42 as shown in FIG. 2.

The system and method of the invention provides a simple system for identifying potential fugitive emission sources, measuring and storing the fugitive emission rate, and correlating the fugitive emission with, for example, previous fugitive emissions from the same source or other sources.

Database software associated with the system eliminates the chances for error inherent in manual input of the data, and allows for database management of the emissions data and its integration with construction and maintenance data. Integration of the databases, as in a relational database, allows use of "as built" or "up dated" drawings to quickly locate each source identified by bar code number.

The database management system and method of the invention also provide a means of comparing fugitive emission rates by commodity, across commodities, by source, across sources for a given time, or by time series for a given source.

The database management system is illustrated in FIGURE 3 which shows three tables. The first table is the SAMPLES Table. The SAMPLES Table allows recovery of sample data by location (barcode), date, time, and attribute, as concentration, shown in PPMV (parts per million by volume). The second table is the SOURCE DESCRIPTER Table. This table allows recovery of system data by location (barcode), and includes such items as the type of equipment, and progressively lower level descripters of the system, i.e., "Plant 1" and "Solvent Recovery," as well as the contents of the stream, here CHCl₃, and operating parameters, here the pressure and temperature.

These tables were used to construct the REPORT Table, here a report for Valve 11000001, which shows the parts per million by volume of CHCl₃ in the vicinity of the valve. The trends shown by this type of comparison could be utilized for predictive maintenance or preventive maintenance.

The relational database could be further integrated with a CAD or engineering database, to relate the barcodes to the locations of the specific hardware within the industrial complex.

While the invention has been described with respect to certain preferred embodiments and exemplifications, it is not intended to limit the scope of the invention thereby, but solely by the claims appended hereto.

I claim:

1. A system for monitoring fugitive volatile organic emissions in an environment having a plurality of fugitive volatile organic emission sources and comprising:
   a. unique machine readable bar code means at each fugitive volatile organic emissions source for identifying the source;
   b. portable monitoring means including:
      (1). reader means, responsive to said unique machine readable bar code means, for reading the machine readable bar code means and generating a machine storable source identification signal responsive thereto;
      (2). organic vapor analyzer detection means for generating a machine storable fugitive volatile organic emissions signal representing the chemical identity and concentration of said fugitive volatile organic emissions from said fugitive volatile organic emissions source; and
      (3). means for storing said source identification signal and said fugitive volatile organic emissions signal; and
   c. computer means including a database management system responsive to said stored source identification signal and said fugitive volatile organic emissions signal, said database management system having means for storing, sorting, tracking and comparing the instantaneous and total amounts of fugitive volatile organic emissions by source, commodity, source parameters including pressure and temperature, and time, and reporting fugitive volatile organic emissions across commodities, by source, across sources for a given time, and b y time series for a given source or sources.

2. A system for monitoring fugitive volatile organic emissions in an industrial complex having a plurality of fugitive volatile organic emission sources and comprising:
   a. unique machine readable bar code means at each fugitive volatile organic emissions source for identifying the source;
   b. portable monitoring means including:
      (1). reader means, responsive to said unique machine readable bar code means, for reading the machine readable bar code means and generating a machine storable source identification signal responsive thereto;
      (2). organic vapor analyzer detection means for generating a machine storable fugitive volatile organic emissions signal representing the chemical identity and concentration of said fugitive volatile organic emissions from said fugitive volatile organic emissions source; and
      (3). means for storing said source identification signal and said fugitive volatile organic emissions signal; and
   c. computer means including a database management system responsive to said stored source identification signal and said fugitive volatile organic emissions signal, said database management system having means for storing, sorting, tracking and comparing the instantaneous and total amounts of fugitive volatile organic emissions by source, commodity, source parameters including pressure and temperature, and time, and reporting fugitive volatile organic emissions across commodities, by source, across sources for a given time, and by time series for a given source or sources, said database management system further including means to relate individual barcodes to specific hardware, the locations of the specific hardware within the industrial complex, and the maintenance and construction history of the specific hardware.

3. A method for monitoring and reporting fugitive volatile organic emissions in an industrial complex, said industrial complex comprising:
   a. a plurality of fugitive volatile organic emission sources, at least some of said sources having a unique machine readable bar code means for uniquely identifying the source;

b. portable monitoring means including:
  (1). reader means, responsive to said unique machine readable bar code means, for reading the machine readable bar code means and generating a machine storable source identification signal responsive thereto;
  (2). organic vapor analyzer detection means for generating a machine storable fugitive volatile organic emissions signal representing the chemical identity and concentration of said fugitive volatile organic emissions from said fugitive volatile organic emissions source; and
  (3). data logger means for storing said source identification signal and said fugitive volatile organic emissions signal; and c. computer means including a database management system responsive to said stored source identification signal and said fugitive volatile organic emissions signal, said database management system having means for storing, sorting, tracking and comparing the instantaneous and total amounts of fugitive volatile organic emissions by source, commodity, source parameters including pressure and temperature, and time, and reporting fugitive volatile organic emissions across commodities, by source, across sources for a given time, and by time series for a given source or sources, said database management system further including means to relate individual barcodes to specific hardware, the locations of the specific hardware within the industrial complex, and the maintenance and construction history of the specific hardware;

said method comprising the steps of:

a. reading the machine readable bar code means at a source and generating a machine storable source identification signal responsive thereto whereby said source is uniquely identified;

b. sampling the volatile organic vapors in the immediate vicinity of said source with the organic vapor analyzer detection means, generating a machine storable fugitive volatile organic emissions signal representing the chemical identity and concentration of said fugitive volatile organic emissions from said fugitive volatile organic emissions source;

c. storing in the data logger said source identification signal and said fugitive volatile organic emissions signal;

d. uploading the stored signals corresponding to the barcode source identification signal and said fugitive volatile organic emissions signal from the data logger to the computer means including a database management system; and e. reporting fugitive volatile organic emissions across commodities, by source, across sources for a given time, time series for a given source or sources, and location, maintenance history, and construction history of a given source within the industrial complex.

* * * * *